United States Patent
Omernick et al.

(10) Patent No.: US 7,720,523 B2
(45) Date of Patent: May 18, 2010

(54) SYSTEM AND METHOD FOR MANAGING POWER DEACTIVATION WITHIN A MEDICAL IMAGING SYSTEM

(75) Inventors: Jon C. Omernick, Wauwatosa, WI (US); Sabih Qamar-Uz Zaman, Elm Grove, WI (US)

(73) Assignee: General Electric Company, Schenectady, NY (US)

( * ) Notice: Subject to any disclaimer, the term of this patent is extended or adjusted under 35 U.S.C. 154(b) by 1197 days.

(21) Appl. No.: 11/180,386

(22) Filed: Jul. 13, 2005

(65) Prior Publication Data

US 2006/0253022 A1 Nov. 9, 2006

Related U.S. Application Data

(60) Provisional application No. 60/673,026, filed on Apr. 20, 2005.

(51) Int. Cl.
A61B 6/00 (2006.01)
H05G 1/56 (2006.01)
(52) U.S. Cl. .................. 600/427; 378/114; 378/98; 378/58; 378/117; 600/437
(58) Field of Classification Search .............. 600/437, 600/438; 601/2
See application file for complete search history.

(56) References Cited

U.S. PATENT DOCUMENTS

| | | | | |
|---|---|---|---|---|
| 4,802,195 A | * | 1/1989 | Wojcienchowski et al. | ..... 378/58 |
| 5,594,771 A | * | 1/1997 | Kawai | ......... 378/98.2 |
| 6,031,888 A | * | 2/2000 | Ivan et al. | ...... 378/20 |
| 6,236,712 B1 | * | 5/2001 | Tomasetti et al. | ........... 378/114 |
| 6,470,207 B1 | * | 10/2002 | Simon et al. | ................. 600/426 |
| 6,809,458 B2 | * | 10/2004 | Matsushita et al. | ...... 310/316.01 |
| 6,986,074 B2 | * | 1/2006 | Alia et al. | .................... 713/601 |
| 2002/0152407 A1 | * | 10/2002 | Alia et al. | .................... 713/300 |
| 2005/0080326 A1 | * | 4/2005 | Mathew | ....................... 600/407 |

* cited by examiner

Primary Examiner—Eric F Winakur
Assistant Examiner—Joel F Brutus
(74) Attorney, Agent, or Firm—McAndrews, Held & Malloy, Ltd.; Peter J. Vogel; Michael A. Dellapenna

(57) ABSTRACT

A medical imaging system includes a medical imaging device, a medical imaging control subsystem, and an activation unit. The medical imaging control subsystem includes a processing unit and a monitor. The processing unit is in communication with the medical imaging device and the monitor. The activation unit is operatively connected to the medical imaging device and the medical imaging control subsystem, wherein the activation unit is operable to deactivate the medical imaging device and the medical imaging control subsystem.

19 Claims, 3 Drawing Sheets

SYSTEM AND METHOD FOR MANAGING POWER DEACTIVATION WITHIN A MEDICAL IMAGING SYSTEM

RELATED APPLICATIONS

This application relates to and claims priority benefits from U.S. Provisional Patent Application No. 60/673,026 entitled "System and Method for Managing Power Deactivation Within a Medical Imaging System," filed Apr. 20, 2005, which is incorporated by reference herein in its entirety.

BACKGROUND OF THE INVENTION

Embodiments of the present invention generally relate to imaging systems, such as medical imaging systems, and more particularly to a system and method of managing power deactivation within a medical imaging system.

Various medical imaging systems and modalities are known and used for diagnosis and assisting in treatment and surgery. For example, ultrasound, magnetic resonance (MR), computed tomography, fluoroscopy and other types of imaging modalities have been used to image various anatomical features.

Various medical imaging systems include a master power device configured for switching a medical imaging system on and off. More particularly, the master power device in some medical imaging systems is a key switch. In order to activate, or "power on", the imaging system, a user inserts a key into the key switch and engages the key into an activation position. In order to deactivate, or "power off," the imaging system, the key is turned to a deactivation position.

Often, an operator is required to separately activate/deactivate each component of an imaging system, such as a medical imaging device and a control unit, such as a computer. Deactivating the control unit abruptly poses several risks. An abrupt deactivation may preclude application software within the control unit from completing a particular task(s), and damage the hard drive. Additionally, separate power/reset switches for multiple components within a system may lead to confusion, and may cause an operator to engage a wrong switch.

Thus, a need exists for a system and method of efficiently deactivating a medical imaging system, including an imaging device that is coupled to a control unit and display. A need also exists for a safer system and method of deactivating a medical imaging system.

SUMMARY OF THE INVENTION

Certain embodiments of the preset invention provide a medical imaging system that includes a medical imaging device, a medical imaging control subsystem, and an activation unit. The medical imaging control subsystem includes a processing unit and a monitor. The processing unit is in communication with the medical imaging device and the monitor. The activation unit is operatively connected to the medical imaging device and the medical imaging control subsystem, wherein the activation unit is operable to deactivate the medical imaging device and the medical imaging control subsystem. The activation unit is also operable to activate the medical imaging device and the medical imaging control subsystem from a deactivated state.

The medical imaging device may be a fluoroscopic C-arm including a main C-shaped body having first and second ends, an x-ray source positioned on the first end, and a detector positioned on the second end, wherein the detector is configured to receive x-rays emitted from the x-ray source. Alternatively, the medical imaging device may be an ultrasound imaging The activation unit may be configured to receive a key. Alternatively, the activation unit may include a button or a switch.

In general, the activation unit is operable to deactivate all components of the medical imaging system, including the medical imaging device and the medical imaging control subsystem, with a single deactivating action, such as through an operator turning a key, or pushing a button.

The medical imaging system may also include a surgical navigation subsystem in communication with the medical imaging control subsystem and the authorization unit. The authorization unit is operable to deactivate the surgical navigation subsystem along with the medical imaging control subsystem and the medical imaging device.

Certain embodiments of the present invention provide a method of deactivating a medical imaging system including operatively connecting an activation unit to a medical imaging device and a medical imaging control subsystem, engaging the activation unit into a deactivation position, and deactivating both the medical imaging device and the medical imaging control subsystem through said engaging. The deactivating step may include reducing power supplied to the medical imaging control subsystem for a set period of time. The method may also include powering off the medical imaging control subsystem if no reactivation event occurs during the set period of time. Conversely, the method may include reactivating the medical imaging control subsystem and interrupting the deactivating step if a reactivation event, such as by engaging an input device or the activation unit, occurs during the set period of time. The deactivating step may also include completely powering off, shutting down, or otherwise turning off, the medical imaging device.

The method may also include deactivating the medical imaging device and the medical imaging control subsystem if the activation unit loses communication with at one or both of the medical imaging device and the medical imaging control subsystem. Additionally, the deactivating step may also include allowing a critical application process to finish before shutting down the imaging control subsystem.

Certain embodiments of the present invention also provide a method of deactivating a fluoroscopic imaging system, which may be a portable x-ray system that runs on battery power. The fluoroscopic imaging system may include a (i) C-arm assembly having a C-shaped body with an x-ray source and a detector mounted thereto and a C-arm operation control unit configured to control movement of the C-shaped body, and (ii) a fluoroscopic imaging control subsystem having an imaging control unit in communication a monitor and the C-arm assembly. The method includes operatively connecting an activation unit to the C-arm assembly and the fluoroscopic imaging control subsystem, engaging the activation unit into a deactivation position, and deactivating both the C-arm assembly and the fluoroscopic imaging control subsystem through the engaging step. The deactivating step includes (i) immediately powering off the C-arm assembly and (ii) reducing power supplied to the fluoroscopic imaging control subsystem for a set period of time.

Figure 1:
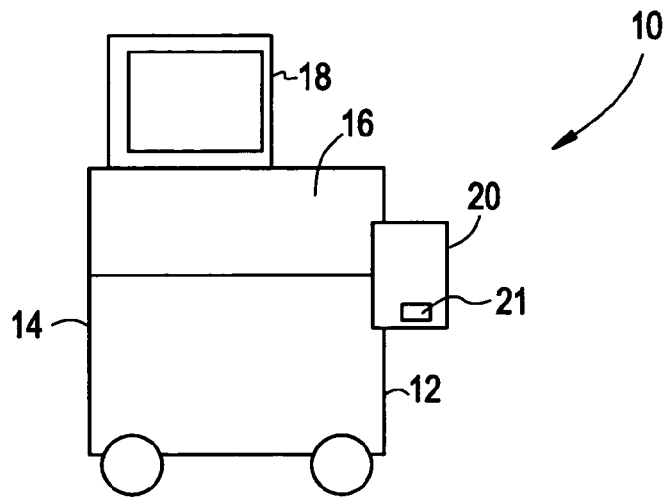
FIG. 1 illustrates a block diagram of an imaging system according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

FIG. 1 illustrates a medical imaging system 10 according to an embodiment of the present invention. The imaging control system 10 includes a main body 12 housing an imaging control unit or central processing unit 14, electronics, and other components, a user control input unit 16 (such as a keyboard, mouse, or touchscreen monitor), an imaging device (such as portable fluoroscopic imaging device, an x-ray C-arm, ultrasound probe, or the like), a display unit 18, and an activation unit 20. The user control input unit 16, the imaging equipment (such as a fluoroscopic, ultrasound, or other such imaging system), the display unit 18 and the activation unit 20 are each in operative electrical communication with the central processing unit 14.

The activation unit 20 is in electrical communication with each component of the medical imaging system 10. For example, the activation unit 20 is in electrical communication with power control processing circuits of each of the display unit 18, the imaging central processing unit 16, and the imaging device, such as an x-ray C-arm. An operator may activate and deactivate the components of the medical imaging system 10 through the activation unit 20. As such, the operator does not have to separately turn on and off each constituent component of the medical imaging system 10. The activation unit 20 includes an interface 21 configured to receive an activating member. For example, the interface 21 may be a keyhole, while the activating member may be a key. Alternatively, the interface 21 may be a button or switch that an operator may engage.

The activation unit 20 may be manufactured as an integral part of the imaging system 10. For example, the activation unit 20 may be integrally formed with the main body 12 of the imaging system, the display unit 18, the imaging control unit 16, or an imaging device, such as an x-ray C-arm, as discussed below. Further, the activation unit 20 may be retrofitted on older imaging systems. For example, the activation unit 20 may be electrically connected to the constituent components of an imaging system, and mounted to the imaging system. Power control software may be programmed into the imaging control unit 16, an operation control unit of an imaging device, and/or a separate processing unit within the activation unit 20 that includes instructions stored in a memory for activating and deactivating the entire imaging system 10 through the activation unit 20.

The imaging system 10 may be an ultrasound system, or it may be various other types of imaging systems, such as a fluoroscopic, MR, or CT imaging system. For example, the imaging system may include an X-ray C-arm having an X-ray source positioned on one distal end of the arm, with a detector positioned on the other distal end of the arm, such as shown and described in U.S. Pat. No. 6,104,780, entitled "Mobile bi-planar fluoroscopic imaging apparatus," U.S. Pat. No. 5,802,719, entitled "One piece C-arm for x-ray diagnostic equipment," and U.S. Pat. No. 5,627,873, entitled "Mini C-arm assembly for mobile x-ray imaging system," all of which are hereby incorporated by reference in their entireties. Optionally, the imaging system may be an MR system, such as described in U.S. Pat. No. 6,462,544, entitled "Magnetic resonance imaging apparatus," which is also hereby incorporated by reference in its entirety.

Figure 1A:
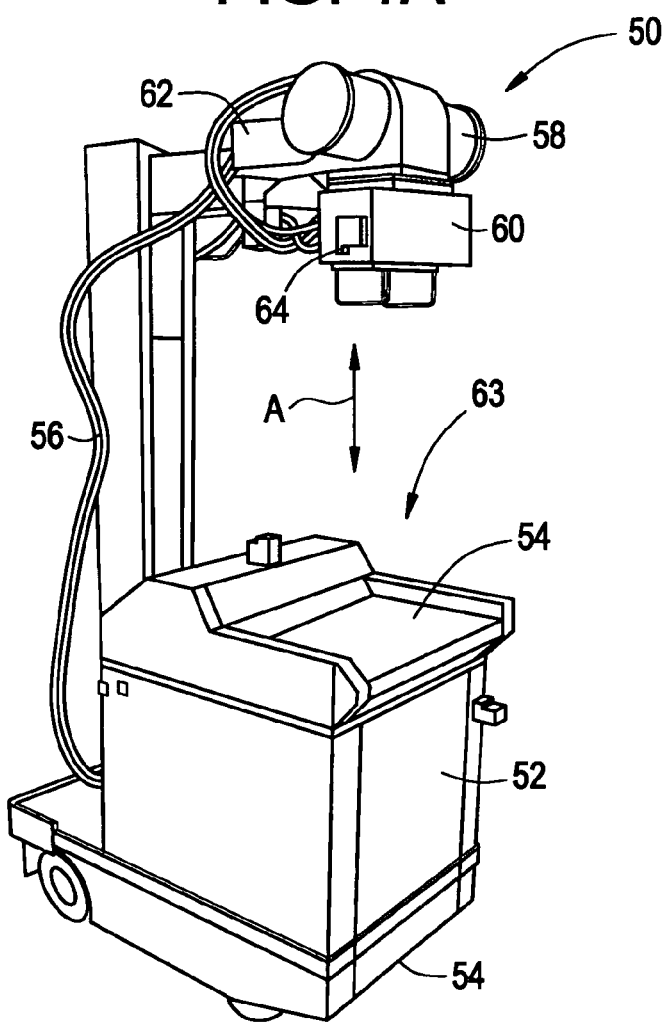
FIG. 1a illustrates an isometric view of a portable x-ray imaging device, according to an embodiment of the present invention.

FIG. 1a illustrates an isometric view of a portable x-ray imaging device 50, according to an embodiment of the present invention. The portable x-ray imaging device 50 may be configured to run on battery power. The x-ray imaging device 50 includes a main body 52 supported by a wheeled support structure 54. The main body 52 includes a base 54 having a detector 54. An upright support 56 extends from the wheeled support structure 54 and/or the base 54 and supports a source assembly 58. The source assembly 58 includes an x-ray source 60 connected to a support 62 that is movably connected to the upright support 56. As such, the x-ray source 60 may be moved relative to the detector 54 over directions indicated by arrow A. An object to be imaged is positioned within an imaging area 63, located between the x-ray detector 54 and the x-ray source 60. The portable x-ray imaging device 50 includes an activation unit, such as the activation unit 20 shown and described in FIG. 1.

Figure 2:
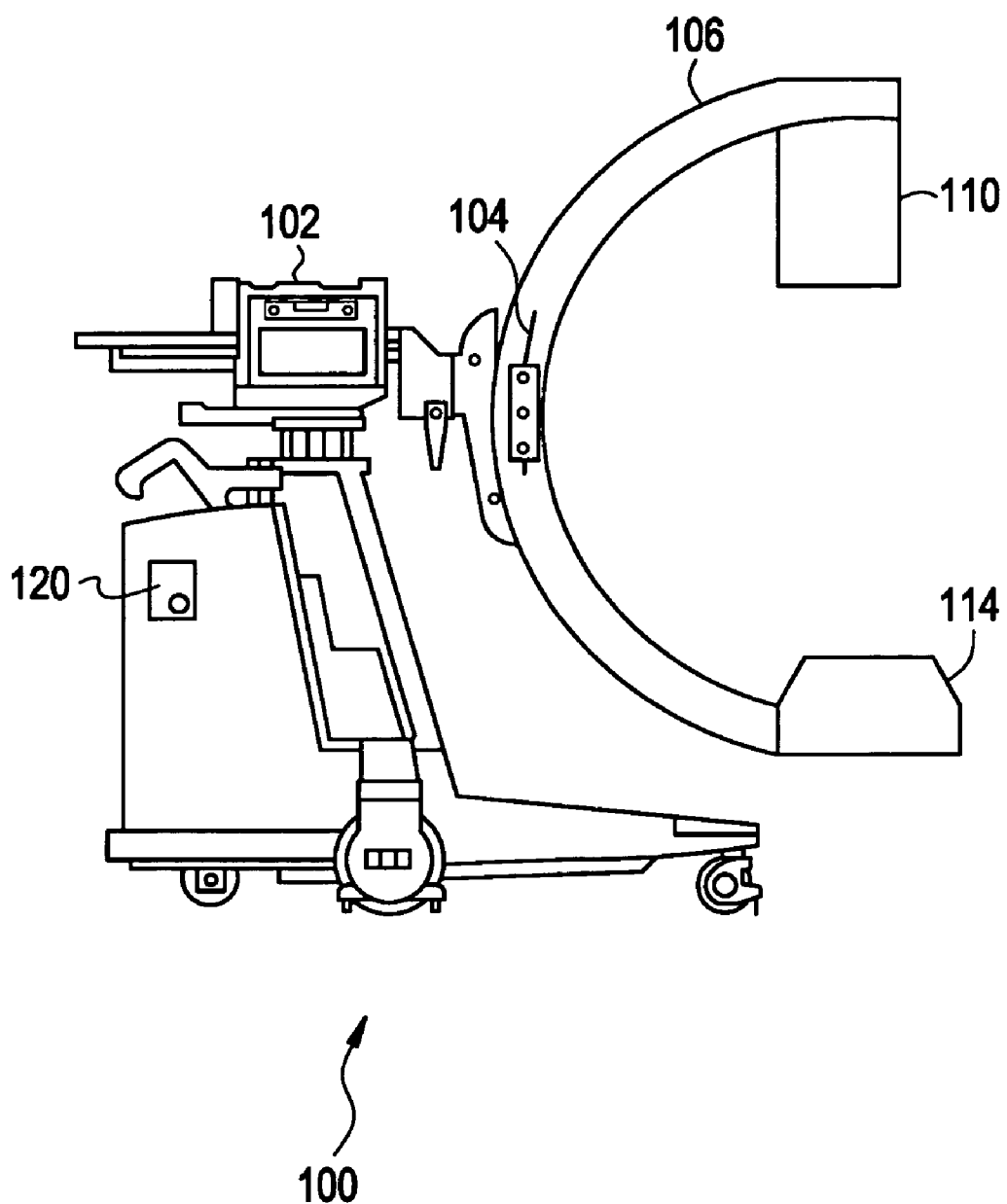
FIG. 2 illustrates a side view of a fluoroscopic imaging system according to an embodiment of the present invention.

FIG. 2 illustrates an x-ray system 100 according to an embodiment of the present invention. The x-ray system 100 includes a mobile support structure 102, a bearing assembly 104 and a positioning arm, or C-arm 106. An x-ray detector 110 is connected to one distal end of the C-arm 106, and an x-ray source 114 is connected to another distal end of the C-arm 106. The x-ray system 100 also includes a control system 120 having processing circuitry that is configured to control activation, operation, and deactivation of the system 100. The control system 120 is in electrical communication with the activation unit 20 shown in FIG. 1, such that the activation unit 20 controls activation, or "powering up", and deactivation, or "powering down", of the system 100. Alternatively, the x-ray system 100 may include its own activation unit 20.

Embodiments of the present invention may be also used with a variety of ultrasound imaging systems. For example, the imaging system 10 shown in FIG. 1 may be an ultrasound imaging system, which may be a two-dimensional, or three-dimensional ultrasound system. Also, the ultrasound systems may be, for example, B-mode, Doppler, or other types of systems known and used in the art. Further, various types of ultrasound probes may be used including probes having sector, linear, curved, or active matrix arrays. Overall, embodiments of the present invention may be used with any type of medical imaging system, including magnetic resonance (MR), computed tomography (CT), fluoroscopic, and the like.

Figure 3:
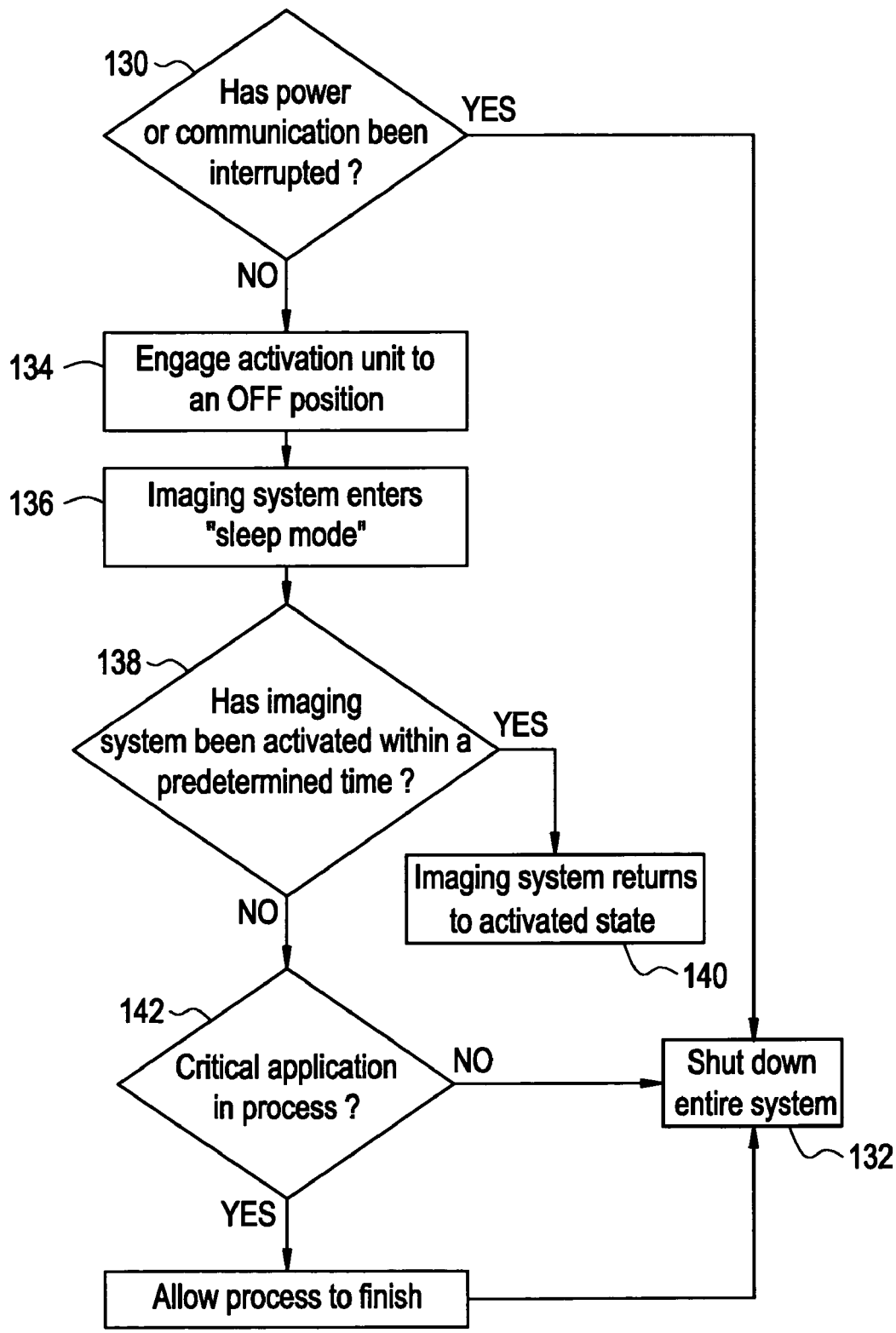
FIG. 3 illustrates a flow chart of a power deactivation process according to an embodiment of the present invention.

FIG. 3 illustrates a flow chart of a power deactivation process according to an embodiment of the present invention. Referring to FIGS. 1 and 3, at 130, a processing unit within an activation unit 20 or imaging control system 14 determines if power or communication to, or within, the system 10 has been interrupted. Communication within the system 10 is interrupted if, for example, the activation unit 20 loses communication with the imaging control system 14 or the imaging device, such as the C-arm 100. Power interruption occurs if the supply of power to the system is blocked, stopped, or otherwise interrupted. In this case, a deactivation program stored within a memory of the medical imaging system 10 is directed to shut down the entire system, including the imaging system and the imaging device (such as a mobile x-ray C-arm), at 132.

If the components of the medical imaging system 10 remain in communication with one another, and if power is being supplied to the medical imaging system 10, the system remains active until an operator decides to deactivate the system. At 134, a user engages the activation unit 20 to an OFF position, if the system 10 is to be deactivated. As discussed above, the user may perform this operation by turning a key or pressing a button, depending on the nature of the activation unit 20.

Once the activation unit 20 is engaged in an OFF position, the imaging system 10 enters a "sleep mode" at 136. In the sleep mode, the power supply to components of the imaging device, such as an x-ray detector, source, and operation control unit of the device, may be turned off, so that those components are deactivated. As such, the system uses a reduced amount of power, which conserves overall power supply, such as battery power. At the same time, the imaging control system 10, including the monitor 18 and the imaging control unit 14, may enter a low power state for a predetermined period of time. In the low power state, power is still being supplied to the imaging control system 10, but at a reduced level. The predetermined period of time may be ten to fifteen seconds, two to three minutes, a few hours, or even a day, depending on how the system 10 is configured to operate. As such, the operator may leave the system 10 in a ready state in which power is conserved. The system 10 can then be fully reactivated from the ready state quickly and easily, which is in contrast to prior systems in which the system would have to be fully rebooted to reactivate after it was turned off. When a reactivation event occurs, the imaging control unit 14 sends a reactivation signal to the medical imaging device, thereby reactivating the medical imaging device (i.e., turning the medical imaging device back on).

During the sleep mode, the system 10 determines if an operator has decided to re-activate the system at 138. For example, the operator may engage the input device 16 (e.g., moving a mouse), or re-engage the activation unit 20. If the operator engages the system to reactivate, the imaging system 10 returns to an activated state, in which full power is supplied to all components of the system at 140.

If, however, the system is not engaged for reactivation, the system determines if a critical application is in process at 142. If a critical application, such as saving imaging data, sending image data to a printer or PACS archival system, or imaging an object of interest, is still in process, the system allows the critical application process to finish at 144. If the system is not engaged in a critical application, or when a critical application finishes, the entire system is deactivated, including the imaging control system, the imaging device, and any other powered components, at 132. As such, power is no longer supplied to any component of the medical imaging system 10.

As mentioned above, embodiments of the present invention may be used with various imaging modalities. For example, the activation unit may be used with Computed Tomography (CT), X-ray (film-based and digital x-ray systems), Positron Emission Tomography (PET), such as shown and described in U.S. Pat. No. 6,337,481, entitled "Data binning method and apparatus for PET tomography including remote services over a network," which is hereby incorporated by reference in its entirety, Single Photon Emission Computed Tomography (SPECT), such as shown and described in U.S. Pat. No. 6,194,725, entitled "SPECT system with reduced radius detectors," which is hereby incorporated by reference in its entirety, Electron Beam Tomography (EBT), such as shown and described in U.S. Pat. No. 5,442,673, entitled "Fixed septum collimator for electron beam tomography," which is hereby incorporated by reference in its entirety, Magnetic Resonance (MR), and various other imaging systems.

Additionally, embodiments of the present invention may also be used with navigation and tracking systems, such as those described in U.S. Pat. No. 5,803,089, entitled "Position Tracking and Imaging System for Use in Medical Applications," which is hereby incorporated by reference in its entirety. For example, the activation unit 20 shown in FIG. 1 may be in communication with a surgical navigation system, in addition to being in communication with an imaging system and imaging device. As such, the activation unit 20 may control activation and deactivation of the imaging system, the imaging device, and the surgical navigation system.

Thus, embodiments of the present invention provide a system and method of efficiently deactivating a medical imaging system, including an imaging device that is coupled to a control unit and display. In general, the embodiments of the present invention provide a safer system and method of deactivating a medical imaging system.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical imaging system, comprising:
a medical imaging device;
a medical imaging control subsystem having a processing unit and a monitor, said processing unit being in communication with said medical imaging device and said monitor; and
an activation unit operatively connected to said medical imaging device and said medical imaging control subsystem, wherein said activation unit is operable to deactivate said medical imaging device and said medical imaging control subsystem with a single deactivation action.

2. The medical imaging system of claim 1, wherein said medical imaging device is a fluoroscopic C-arm comprising:
a main C-shaped body having first and second ends;
an x-ray source positioned on said first end; and
a detector positioned on said second end, wherein said detector is configured to receive x-rays emitted from said x-ray source.

3. The medical imaging system of claim 1, wherein said medical imaging device is an ultrasound imaging device.

4. The medical imaging system of claim 1, wherein said activation unit is configured to receive a key.

5. The medical imaging system of claim 1, wherein said activation unit includes one of a button and a switch.

6. The medical imaging system of claim 1, wherein said activation unit is also operable to activate said medical imaging device and said medical imaging control subsystem from a deactivated state.

7. The medical imaging system of claim 1, comprising a surgical navigation subsystem in communication with said medical imaging control subsystem and said activation unit, wherein said activation unit is operable to deactivate said surgical navigation subsystem along with said medical imaging control subsystem and said medical imaging device.

8. A method of deactivating a medical imaging system, comprising:
operatively connecting an activation unit to a medical imaging device and a medical imaging control subsystem;
engaging the activation unit into a deactivation position; and
deactivating both the medical imaging device and the medical imaging control subsystem through said engaging.

9. The method of claim 8, wherein said deactivating comprises reducing power supplied to the medical imaging control subsystem for a set period of time.

10. The method of claim 9, comprising powering off the medical imaging control subsystem if no reactivation event occurs during the set period of time.

11. The method of claim 9, comprising reactivating the medical imaging control subsystem and interrupting said deactivating if a reactivation event occurs during the set period of time.

12. The method of claim 8, wherein said deactivating comprises powering off the medical imaging device.

13. The method of claim 8, further comprising immediately deactivating the medical imaging device and the medical imaging control subsystem if the activation unit loses communication with at least one of the medical imaging device and the medical imaging control subsystem.

14. The method of claim 8, wherein said deactivating comprises allowing a critical application process to finish before shutting down the imaging control subsystem.

15. The method of claim 8, wherein said deactivating comprises turning a key.

16. A method of deactivating a fluoroscopic imaging system, said fluoroscopic imaging system comprising a (i) C-arm assembly having a C-shaped body with an x-ray source and a detector mounted thereto and a C-arm operation control unit configured to control movement of the C-shaped body, and (ii) a fluoroscopic imaging control subsystem having an imaging control unit in communication a monitor and the C-arm assembly, the method comprising:
operatively connecting an activation unit to the C-arm assembly and the fluoroscopic imaging control subsystem;
engaging the activation unit into a deactivation position; and
deactivating both the C-arm assembly and the fluoroscopic imaging control subsystem through said engaging, wherein said deactivating comprises (i) immediately powering off the C-arm assembly and (ii) reducing power supplied to the fluoroscopic imaging control subsystem for a set period of time.

17. The method of claim 16, comprising powering off the fluoroscopic imaging control subsystem if no reactivation event occurs during the set period of time.

18. The method of claim 16, comprising immediately deactivating the C-arm assembly and the fluoroscopic imaging control subsystem if the activation unit loses communication with at least one of the C-arm assembly and the fluoroscopic imaging control subsystem.

19. The method of claim 16, wherein said deactivating comprises allowing a critical application process to finish before shutting down the fluoroscopic imaging control subsystem.

* * * * *